United States Patent
Kucklick

(10) Patent No.: US 7,503,893 B2
(45) Date of Patent: Mar. 17, 2009

(54) ANTI-EXTRAVASATION SHEATH AND METHOD

(75) Inventor: Theodore R. Kucklick, Los Gatos, CA (US)

(73) Assignee: Cannuflow, Inc., San Jose, CA (US)

( * ) Notice: Subject to any disclaimer, the term of this patent is extended or adjusted under 35 U.S.C. 154(b) by 265 days.

(21) Appl. No.: 11/346,764

(22) Filed: Feb. 3, 2006

(65) Prior Publication Data

US 2007/0185380 A1    Aug. 9, 2007

(51) Int. Cl.
*A61B 1/015* (2006.01)

(52) U.S. Cl. .................. 600/114; 600/105; 600/156; 604/28

(58) Field of Classification Search ............. 600/105, 600/156, 114; 604/28, 30, 35, 256
See application file for complete search history.

(56) References Cited

U.S. PATENT DOCUMENTS

| | | | | |
|---|---|---|---|---|
| 4,950,278 A | * | 8/1990 | Sachse et al. | 606/170 |
| 4,959,058 A | * | 9/1990 | Michelson | 604/523 |
| 5,171,223 A | * | 12/1992 | Herzberg | 604/104 |
| 5,320,091 A | * | 6/1994 | Grossi et al. | 600/104 |
| 5,527,276 A | * | 6/1996 | Bruce | 604/506 |
| 5,800,409 A | * | 9/1998 | Bruce | 604/523 |
| 5,807,240 A | * | 9/1998 | Muller et al. | 600/135 |
| 6,024,720 A | * | 2/2000 | Chandler et al. | 604/35 |
| 6,086,542 A | * | 7/2000 | Glowa et al. | 600/561 |
| 6,428,510 B1 | * | 8/2002 | Kadan | 604/164.04 |
| 7,150,713 B2 | * | 12/2006 | Shener et al. | 600/156 |
| 2003/0014050 A1 | * | 1/2003 | Sharkey et al. | 606/45 |
| 2003/0050603 A1 | * | 3/2003 | Todd | 604/164.02 |
| 2003/0130565 A1 | | 7/2003 | Muller | |
| 2003/0171664 A1 | * | 9/2003 | Wendlandt | 600/407 |
| 2005/0043682 A1 | * | 2/2005 | Kucklick et al. | 604/164.09 |
| 2005/0043690 A1 | * | 2/2005 | Todd | 604/248 |
| 2005/0171470 A1 | | 8/2005 | Kucklick et al. | |
| 2005/0203342 A1 | * | 9/2005 | Kucklick et al. | 600/156 |
| 2005/0234298 A1 | | 10/2005 | Kucklick et al. | |
| 2006/0047184 A1 | * | 3/2006 | Banik et al. | 600/156 |
| 2006/0047185 A1 | * | 3/2006 | Shener et al. | 600/156 |

* cited by examiner

*Primary Examiner*—John P Leubecker
(74) *Attorney, Agent, or Firm*—Susan L. Crockett, Esq.; Crockett & Crockett

(57) ABSTRACT

The methods shown provide for the minimization of extravasation during arthroscopic surgery. Use of an anti-extravasation sheath having at least one drainage aperture allows a surgeon to drain excess fluids from the tissue surrounding the surgical field during an arthroscopic surgical procedures when the drainage aperture is disposed within the tissue surrounding an arthroscopic surgical field outside of the joint capsule. The method of performing arthroscopic surgery may further include providing fluid inflow and outflow to the joint capsule through inflow/outflow holes in the anti-extravasation sheath.

3 Claims, 8 Drawing Sheets

ANTI-EXTRAVASATION SHEATH AND METHOD

FIELD OF THE INVENTIONS

The inventions described below relate to the field arthroscopic surgery and more specifically, to fluid management during arthroscopic shoulder surgery.

BACKGROUND OF THE INVENTIONS

During minimally invasive surgeries, surgical instruments such as trocars, cannulas, and optical medical devices, including endoscopes, cystoscopes, arthroscopes, laparoscopes, etc., are inserted through small incisions or portals in a patient's body or body cavity and manipulated to perform surgical procedures within the patient.

Minimally invasive surgical procedures are safer than open surgery and result in quicker patient recovery, shorter hospital stays, and lower health care costs. Accordingly, minimizing invasiveness continues to be of importance, and there is a continuing need for devices and methods that achieve this objective.

One area that has benefited from minimally invasive surgical techniques is shoulder surgery. Shoulder surgery has evolved over the last several years from being an open surgical procedure to an arthroscopic surgical procedure. This evolution is the result of technological advances in equipment, instruments and implants.

During surgery, fluid is introduced into the surgical site of field to expand the joint and control bleeding. A major concern involving arthroscopic surgery of the shoulder is extravasation. Extravasation is the collection of interstitial fluid such as blood, irrigation fluids or medications into tissue surrounding an infusion site. Fluid escaping into the soft tissues of the shoulder and the periscapular region can have adverse effects on the patient. Some of these effects include tracheal compression, the accumulation of blood or clots in the joint (hemarthrosis), the forming of blood clots in veins (thrombophlebitis), arterial injury, nerve injury, the compression of blood vessels and nerves surrounding the joint (compartment syndrome), and infection. These effects cause longer recovery time as well as pain and discomfort in patients. Extravasation occurring during surgery can also cause premature collapse of the surgical field forcing surgeons to rush procedures. Because of the effects caused by extravasation, devices and methods are needed to reduce extravasation during arthroscopic shoulder surgery.

SUMMARY

The devices and methods shown below provide for the minimization of fluid extravasation during arthroscopic surgery. The anti-extravasation inflow/outflow sheath allows a surgeon to drain fluids from the soft tissue surrounding the surgical field while also providing fluid inflow and outflow to a surgical site.

The anti-extravasation inflow/outflow sheath is a multi-lumen tube into which an arthroscopic surgical instrument such as an arthroscope is inserted. The proximal portion of the sheath is provided with fluid ports, a manifold and other means of controlling the flow of fluid inside the sheath. The distal portion of the inflow/outflow sheath is provided with a plurality of inflow/outflow holes. The body or central portion of the sheath is provided with a plurality of drainage apertures. Each inflow/outflow hole communicates with one or more of the lumens inside the tube, thereby allowing fluid to flow between the surgical field and sources or sinks located outside the patient. Each drainage aperture communicates with one or more of the drainage lumens inside the tube, thereby allowing fluid to drain from the tissue surrounding the surgical site and sources or sinks located outside the patient. The anti-extravasation inflow/outflow sheath allows the surgeon to maintain a clear surgical field and eliminate the need for a third irrigation instrument while reducing the amount of fluid extravasation occurring in surrounding tissue.

DETAILED DESCRIPTION OF THE INVENTIONS

Figure 1:
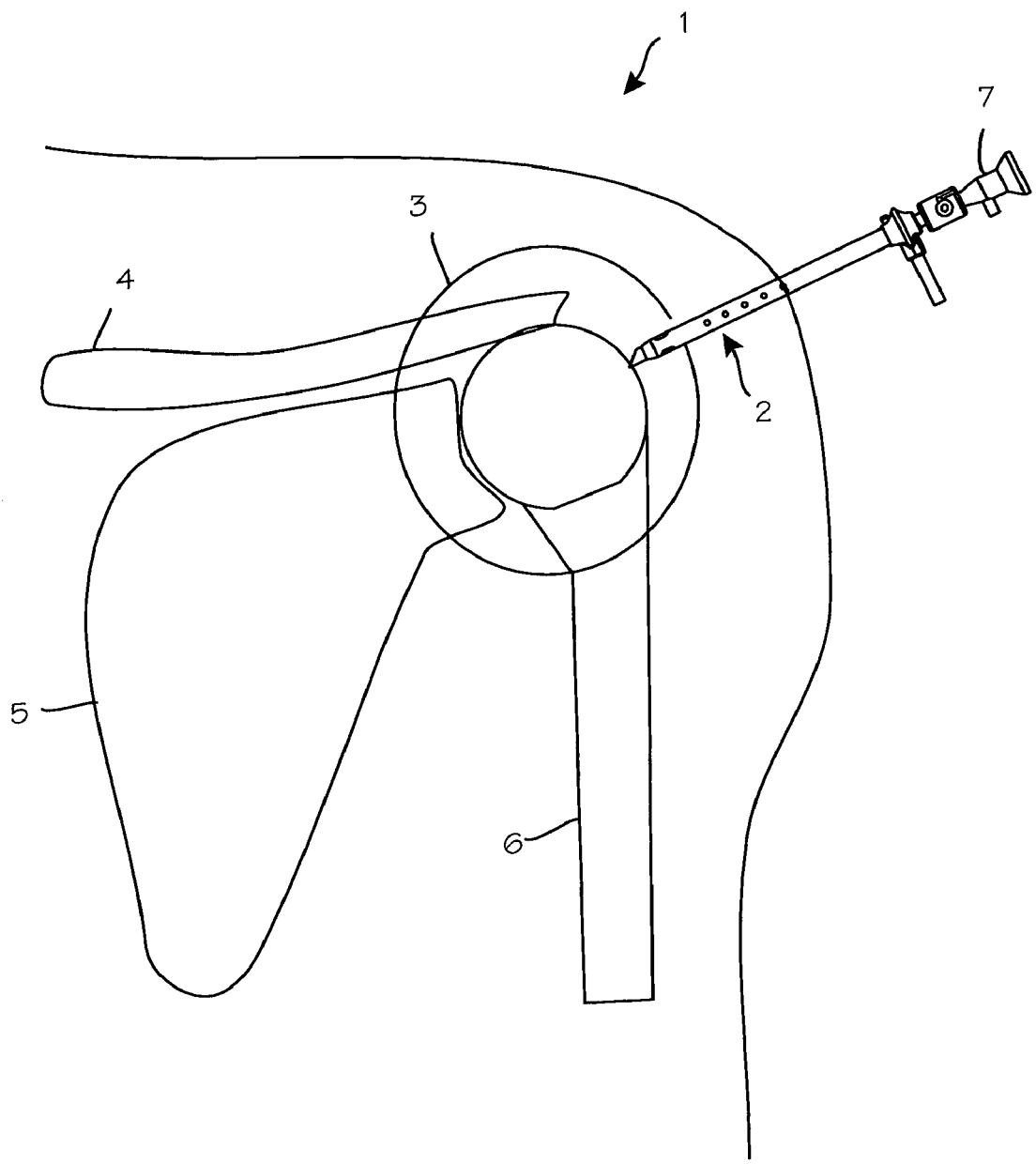
FIG. 1 illustrates a method of performing arthroscopic surgery on a patient using the anti-extravasation inflow/outflow sheath.

FIG. 1 illustrates a method of performing arthroscopic surgery on a patient's shoulder 1 using the anti-extravasation sheath 2. The anti-extravasation sheath is shown inserted into the joint capsule 3 of a shoulder of a patient. Various anatomical landmarks are depicted including the patient's clavicle 4, scapula 5 and humerus 6. An arthroscopic instrument 7 such as an arthroscope is disposed within the anti-extravasation sheath.

During arthroscopic shoulder surgery, the surgeon introduces the arthroscope into the shoulder via a first portal in order to visualize the surgical field. A trimming instrument is introduced through a second portal to remove or trim tissue that the surgeon determines should be removed or trimmed. Optionally, an irrigating instrument may be introduced through a third portal in order to distend the joint, and/or irrigate the surgical field to maintain a clear view. Other arthroscopic instruments used in arthroscopic surgery include endoscopes, awls, picks or shavers.

Figure 2:
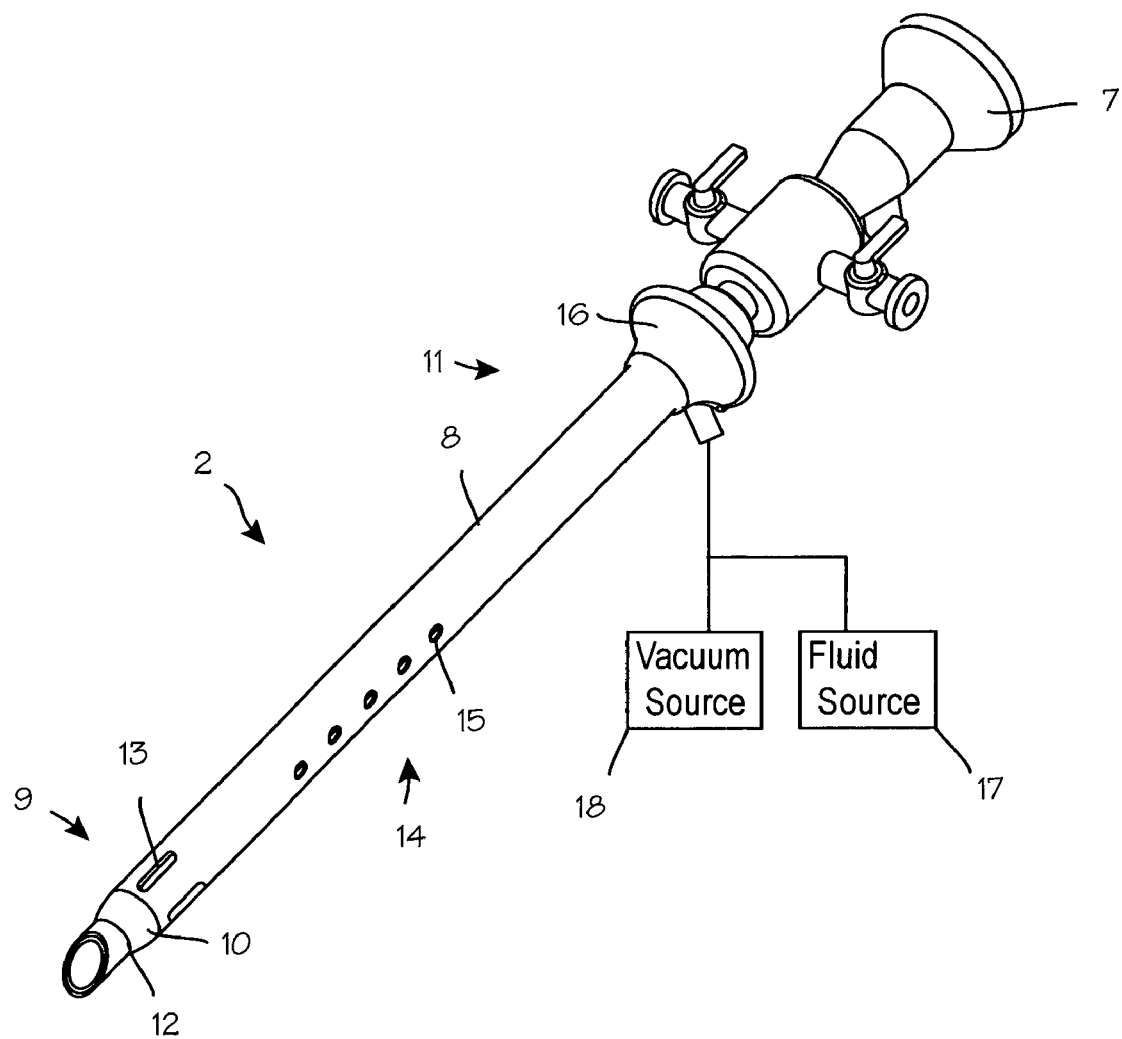
FIG. 2 illustrates the anti-extravasation sheath with inflow/outflow holes or apertures disposed on the distal section of the sheath.

FIG. 2 illustrates the anti-extravasation sheath with inflow/outflow holes or apertures disposed on the distal section of the sheath. The anti-extravasation sheath is a tube 8 of resilient material such as nylon, polycarbonate urethane, polyurethane, polydimethylsiloxane and polyethylene glycol or rubber, characterized by a central lumen. The inner diameter of the atraumatic sheath is sized and dimensioned to closely fit over the outer diameter of an arthroscopic instrument. The tube 8 is characterized by a distal section 9 having a distal tip 10 and a proximal section 11. The distal tip 10 of the tube is provided with a frustoconical shape and an opening 12 that is slightly smaller in diameter than the outer diameter of the distal tip of the arthroscope and/or the rigid cannula or other surgical instrument. Alternatively, the tip 10 may have an arcuate cross-section. The opening is provided in the sheath so the surgeon may insert the endoscope, or other surgical instruments, through the opening and into the surgical space. The distal section 9 of the sheath further comprises inflow/outflow holes 13, openings or apertures that may be placed in fluid communication with a fluid source or vacuum source outside the patient. The inflow/outflow holes 13 provide for fluid flow to and from the joint capsule or surgical field. The body or central portion 14 of the tube is provided with a plurality of drainage apertures 15. The drainage apertures 15 are disposed in such a way that they are placed in fluid communication with tissue surrounding a joint capsule 3 or surgical field when the sheath is in use. Each drainage aperture 15 communicates with one or more drainage lumens disposed inside the tube, thereby allowing fluid to drain from the tissue surrounding the capsule 3 to sources or sinks located outside the patient. The proximal section of the sheath is provided with a hub 16 manufactured from an elastomer to allow medical personnel to easily pull the atraumatic sheath over and secure the sheath to the rigid cannula, arthroscope and/or arthroscopic instrument. The hub can be adapted for coupling to a fluid source 17, vaccum source 18 or an ergonomic handle. The proximal section of the anti-extravasation sheath may also be provided with fittings, such as a locking hub or snap latches, that attach to fittings or openings disposed on the arthroscope or other instrument, thereby securing the sheath 2.

The outer surface of the anti-extravasation sheath 2 may be provided with a smooth coating to allow the arthroscope and rigid cannula to more easily move within an operating site. For example, the sheath 2 may be provided with a Teflon® (PTFE or expanded polytetrafluoroethylene) coating or covered with a water-activated lubricant. In contrast, the inner surface of the sheath 2 (the walls that define the lumen of the tube) may be provided with a non-slip coating or other high coefficient of friction coating. For example, the inner surface of the sheath 2 may be coated with a co-extruded tacky thermoplastic elastomer (TPE). The non-slip coating prevents the sheath from easily slipping over the outer surface of the rigid cannula or arthroscope, thereby helping to prevent the atraumatic sheath from twisting or slipping around the arthroscope.

The arthroscope 7 is extended distally out of the opening 12 and the surgical space visualized. Inflow/outflow holes 13 or apertures are provided in the distal portion of the sheath. The inflow/outflow holes 13 communicate with one or more inflow/outflow outer lumens in the sheath. The outer lumen or lumens communicate with a vacuum source, fluid source, therapeutic agent source or a combination of sources. Thus, the inflow/outflow holes provide for the inflow and outflow of fluids to the surgical field during a surgical procedure.

The tube of the sheath and the distal tip are manufactured from the same flexible sterilizable polymer. Alternatively, the distal tip of the inflow/outflow atraumatic sheath can be made of an elastic material having a higher modulus of elasticity than the modulus of elasticity found in the material of the proximal portion of the sheath. The distal tip of the sheath has an inner diameter that is slightly smaller than the outer diameter of most arthroscopes.

When the sheath 2 is in use, a user inserts the arthroscope 7 into the sheath 2. The distal tip expands as the distal end of the arthroscope slides past the distal tip of the sheath. Because the inner diameter of the tip is less than the outer diameter of the arthroscope, the tip will form a seal with the outer surface of the arthroscope.

Figure 3:
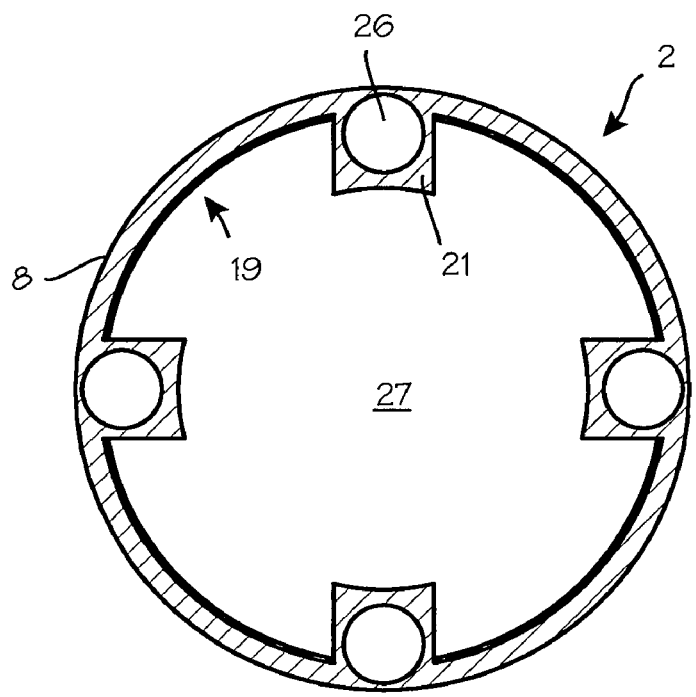
FIG. 3 shows a radial cross-sectional view of the anti-extravasation sheath.
Figure 4:
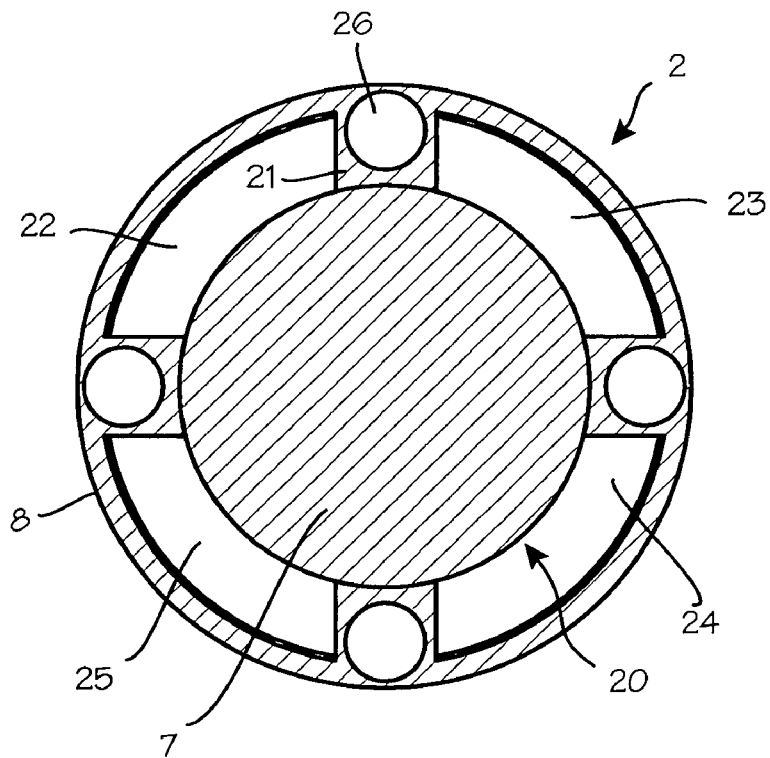
FIG. 4 shows a radial cross-sectional view of the anti-extravasation sheath with an arthroscope disposed within the sheath.

FIG. 3 shows a radial cross-sectional view of the anti-extravasation sheath 2 while FIG. 4 shows a radial cross-sectional view of the anti-extravasation sheath 2 with an arthroscope disposed within the sheath 2. The sheath 2 uses the inner surface 19 of the wall of the tube with the outer surface 20 of the arthroscope to form inflow and outflow outer lumens. A raised distinct tract, also referred to as a land, or relatively stiff ribs 21 extending radially from the inner surface of the outer wall and running longitudinally along the sheath form a seal with the outer surface 20 of the arthroscope, thereby creating the four outer lumens 22, 23, 24, and 25. One or more drainage apertures 15 are disposed on the outer surface of the body or central portion of the tube. The drainage apertures 15 are in fluid communication with the one or more drainage lumens 26 disposed within the ribs 21. The drainage lumens 26 run longitudinally along the sheath and are sized and dimensioned to accommodate fluid outflow from tissue surrounding a joint capsule or surgical field. In alternative embodiments of the sheath, drainage apertures may also be placed in fluid communication with one or more of the outer lumens. The size of the drainage apertures can be used to control the percolation rate of the sheath. The ends of the ribs may be provided with elastic flanges or extensions to enhance the seal made between the ribs and the arthroscope.

As depicted in FIG. 4, the arthroscope is inserted into the sheath through the central lumen 27 of the sheath. The arthroscope may or may not be covered by a secondary protective sheath prior to insertion. Once inserted, the outer surface of the arthroscope comes in contact with the ribs 21. The force of the outer surface of the arthroscope pushing against the ribs and the outer surface of the arthroscope. Outer lumens 22, 23, 24 and 25 are created by the ribs, the outer surface of the endoscope, and inner surface of the outer wall of the anti-extravasation sheath. The ribs act as longitudinal struts that prevent the sheath from collapsing as they support the sheath under compression. The ribs reduce the unsupported span of the thin outer wall in the traverse axis, further preventing the collapse of the sheath. The seals formed by the contact between the ribs and the outer surface of the arthroscope prevent fluids from flowing between the outer lumens 22, 23, 24 and 25. The outer lumens 22, 23, 24 and 25 facilitate the substantially continuous inflow and/or outflow of fluids to and from a joint capsule or surgical field through the inflow/outflow holes in the distal section of the sheath. Check valves or gates may also be coupled to the inner surface of the inflow/outflow sheath within the outer lumens 22, 23, 24 and 25 to prevent outflow fluids from flowing back towards the surgical site and to prevent inflow fluids from flowing out the proximal end of the sheath. The drainage lumens facilitate the outflow of interstitial fluids from tissue surrounding the joint capsule.

During arthroscopic surgical procedures, pressurized fluid flowing through the inflow/outflow holes is used to distend the joint, irrigate the joint capsule, surgical field or surgical site and disrupt tissue bleeding. The pressurized fluid, blood and debris are drained from shoulder tissue surrounding the surgical site through the drainage apertures in the sheath. Removal of fluid, blood and debris reduces the amount of fluid left in the shoulder tissue during arthroscopic shoulder surgery thereby minimizing extravasation. To minimize extravasation, the percolation rate of the extravasation minimization device is greater than the percolation rate of the surrounding tissue. The difference in percolation rates is preferably about 10% to about 15% helping to maintain pressure in the joint during surgery.

The anti-extravasation sheath depicted in FIGS. 2-4 typically has an outer diameter measuring about 5 to 8 millimeters when the sheath is manufactured for use with arthroscopic instruments in larger joints, though this size may vary depending on the diameter of the arthroscopic instrument. When the inflow/outflow sheath is manufactured for use with arthroscopic instruments in smaller joints, the sheath has an outer diameter measuring about 2 to 5 millimeters. The outer wall thickness of the inflow/outflow sheath is typically 1 millimeter or less depending on the extrusion and material comprising the tube. The inflow/outflow sheath can fit a range of arthroscopes +/−10% of the sheath's nominal diameter. The ribs extend from the inner surface of the anti-extravasation sheath inwardly and make a tight fit when the arthroscope is inserted and may hold the arthroscope concentrically in the sheath.

Figure 5:
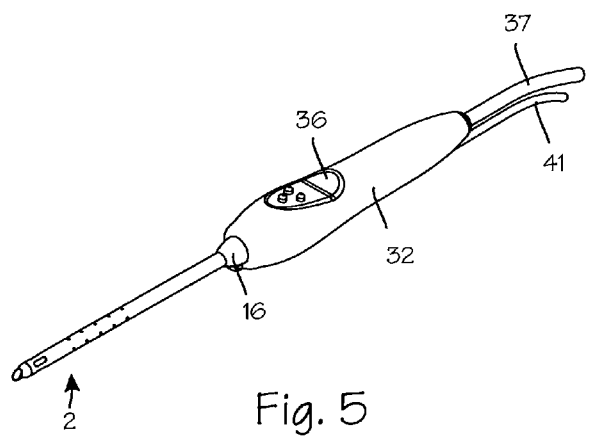
FIG. 5 illustrates an anti-extravasation sheath in use with an ergonomic handle and arthroscope.
Figure 6:
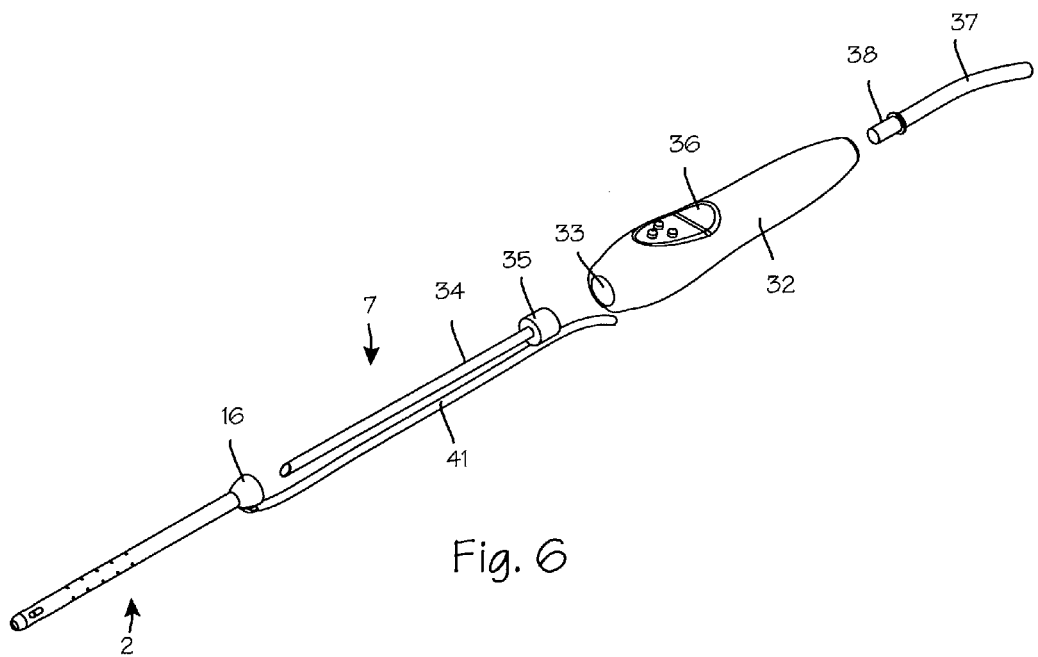
FIG. 6 illustrates an exploded view of the anti-extravasation sheath, arthroscope and ergonomic handle.
Figure 7:
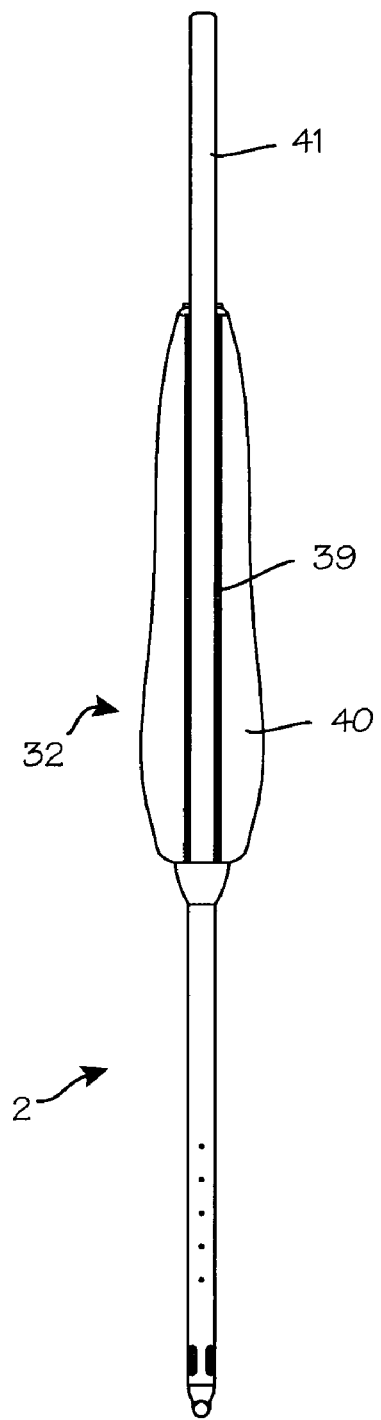
FIG. 7 illustrates a bottom view of an anti-extravasation sheath in use with an ergonomic handle and arthroscope.

The anti-extravasation sheath 2 and arthroscope 7 may be used in conjunction with an ergonomic handle 32 as depicted in FIGS. 5, 6 and 7. FIG. 5 illustrates an anti-extravasation sheath in use with an ergonomic handle and arthroscope while FIG. 6 illustrates an exploded view of the anti-extravasation sheath, arthroscope and ergonomic handle. The handle comprises a receiver 33 for receiving the proximal end of an arthroscope 7 with a rigid cannula 34 having an adapter 35. The handle and the sheath are releasably coupled by a hub 16 at the proximal section of the sheath through snap fitting or friction fitting. The handle is provided with a user interface and control system 36 that may be operably connected to the arthroscope and a fluid management system such as an arthroscopic fluid pump. The control system may be used to regulate fluid flow in and out of the sheath when the sheath is coupled to the handle. The control system 36 may also be used to control focusing of the arthroscope when the arthroscope 7 is operably coupled to the handle 32. Optical cable 37 and electrical cable are operably coupled to the proximal portion of the handle through an optical and electrical coupling 38.

FIG. 7 illustrates a bottom view of an anti-extravasation sheath in use with an ergonomic handle and arthroscope. The handle 32 further comprises a longitudinal channel 39 disposed in its bottom portion 40. The longitudinal channel is sized and dimensioned to accommodate an inflow/outflow tube 41 operably connected to the sheath. The tube 41 friction fits into the channel 39. The channel provides for tubing to be routed substantially below a users wrist and not routed to the side of a user's wrist as in prior art sheaths and arthroscopes.

Figure 8:
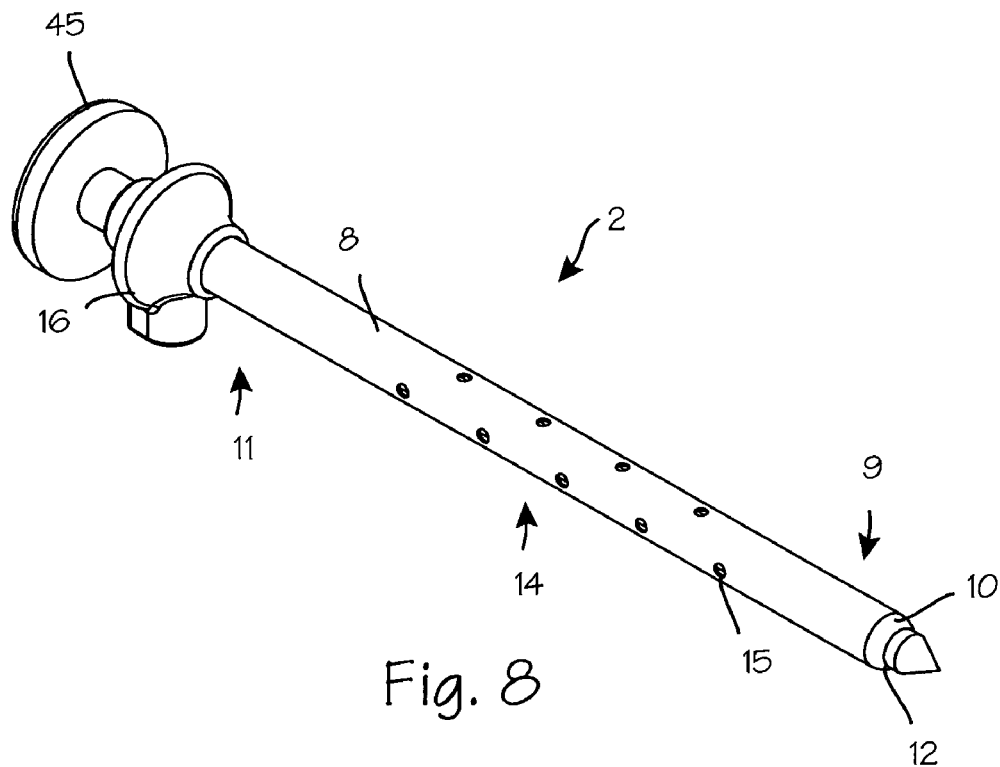
FIG. 8 depicts an anti-extravasation sheath disposed over an obturator.

FIG. 8 depicts an anti-extravasation sheath or cannula disposed over an obturator 42. The anti-extravasation sheath 2 is a tube of resilient material 8 polymer such as nylon, polycarbonate urethane, polyurethane, polydimethylsiloxane and polyethylene glycol or rubber, characterized by a central lumen. The inner diameter of the atraumatic sheath is sized and dimensioned to closely fit over the outer diameter of the obturator. The tube is characterized by a distal section 9 having a distal tip 10 and a proximal section 11. The distal tip of the atraumatic sheath is provided with a frustoconical shape and an opening 12 that is slightly smaller in diameter than the outer diameter of the distal tip of the arthroscope and/or the rigid cannula or other surgical instrument. Alternatively, the tip may have an arcuate cross-section. The opening 12 is provided in the sheath so the surgeon may insert the obturator. The body or central portion 14 of the tube is provided with a plurality of drainage apertures 15 in a series of linear arrays. Each drainage aperture communicates with one or more of the drainage lumens disposed inside the tube, thereby allowing fluid to drain from the tissue surrounding the surgical site to sources or sinks located outside the patient. The proximal section 11 of the sheath is provided with a hub 16 manufactured from an elastomer to allow medical personnel to easily pull the atraumatic sheath over and secure the sheath to the obturator, arthroscope and/or arthroscopic instrument. Further, the hub can be adapted for coupling to a fluid source, a vacuum source or an ergonomic handle. The proximal section of the anti-extravasation sheath may also be provided with fittings, such as a locking hub or snap latches, that attach to fittings or openings disposed on the arthroscope or other instrument, thereby securing the sheath.

Figure 9:
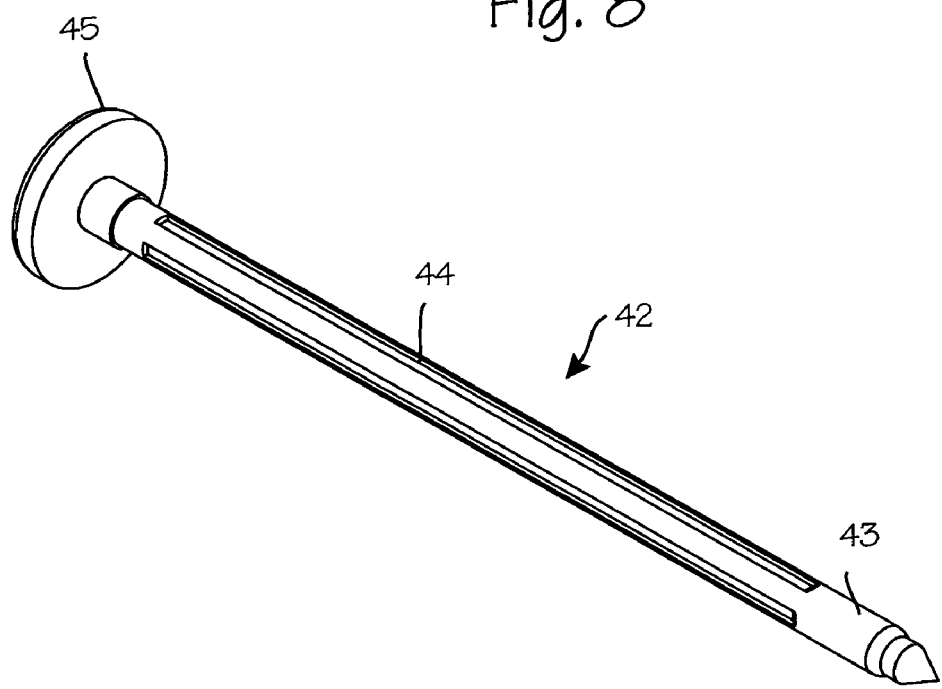
FIG. 9 illustrates an obturator for use in conjunction with a anti-extravasation sheath.

FIG. 9 illustrates an obturator 42 for use in conjunction with a anti-extravasation sheath. The obturator comprises a cylindrical shaft 43 having one or more grooves, channels or flutes 44 disposed longitudinally along the obturator's outer surface. The obturator is provided with a handle 45 disposed on its proximal end. The handle may be used to rotate the obturator when the obturator is disposed in the sheath. The obturator may also be provided with a center lumen allowing the obturator to slide over a rod or guide wire.

Figure 10:
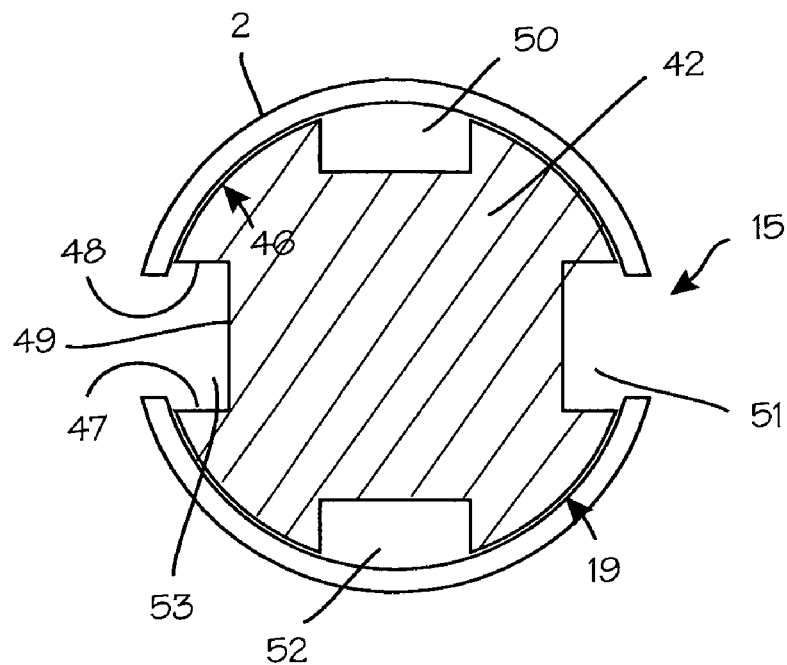
FIG. 10 shows a radial cross-sectional view of the anti-extravasation sheath using the inner surface of the tube wall with the outer surface of the obturator to form outer drainage lumens.

FIG. 10 shows a radial cross-sectional view of the anti-extravasation sheath using the inner surface of the tube wall with the outer surface of the obturator 42 to form outer drainage lumens. The inner surface of the wall 19 of the tube and the outer surface 46 of the obturator forms a seal and the side walls 47,48 and bottom walls 49 of the flutes and the wall of the tube create the longitudinal outer drainage lumens 50, 51, 52 and 53. One or more drainage apertures 15 are disposed on the outer surface of the body or central portion of the sheath. The drainage apertures 15 are in fluid communication with the one or more drainage lumens 50, 51, 52 and 53. The drainage lumens 50, 51, 52 and 53 run longitudinally along the sheath and are sized and dimensioned to accommodate fluid outflow from tissue surrounding a surgical site. The size of the drainage apertures 15 can be used to control the percolation rate of the sheath.

Figure 11:
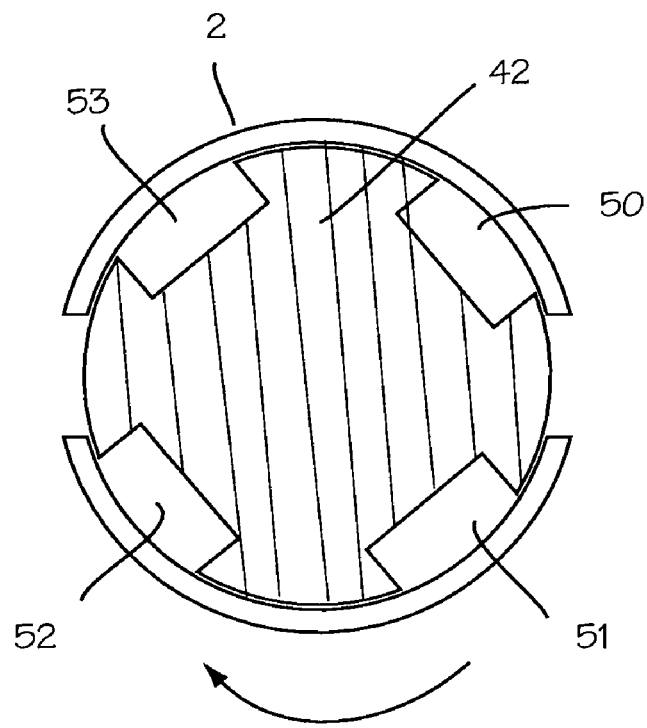
FIG. 11 shows an anti-extravasation sheath disposed over an obturator with the obturator rotated.

When the sheath is in use, a user inserts the obturator into the sheath. The distal tip expands as the distal end of the arthroscope slides past the distal tip of the sheath. Because the inner diameter of the tip is less than the outer diameter of the arthroscope, the tip will form a seal with the outer surface of the arthroscope. The channels are substantially aligned with the arrays of fluid apertures. When a user wants to stop or reduce the outflow of fluid from tissue surrounding the surgical field through the sheath 2, the user can rotate the obturator 42 and misalign the flutes 44 with the arrays of fluid apertures 15 as shown in FIG. 11.

The obturator 42 or other arthroscopic surgical instrument having longitudinal grooves 44 is inserted into the sheath through the central lumen. The obturator 42 may or may not be covered by a secondary protective sheath prior to insertion. Once inserted, the outer surface of the obturator 46 comes in contact with the inner surface of the sheath 19. The force of the outer surface 46 of the obturator pushes against the inner surface of the sheath 19. Outer drainage lumens 50, 51, 52 and 53 are created by the flutes 44 and the inner surface 19 of the outer wall of the anti-extravasation sheath 2. The seals formed by the contact between the sheath and the outer surface of the obturator prevent fluids from flowing between the outer drainage lumens 50, 51, 52 and 53. The outer drainage lumens 50, 51, 52 and 53 facilitate the outflow of fluids from tissue surrounding a surgical site through the drainage apertures 15 in the central portion of the sheath.

Figure 12:
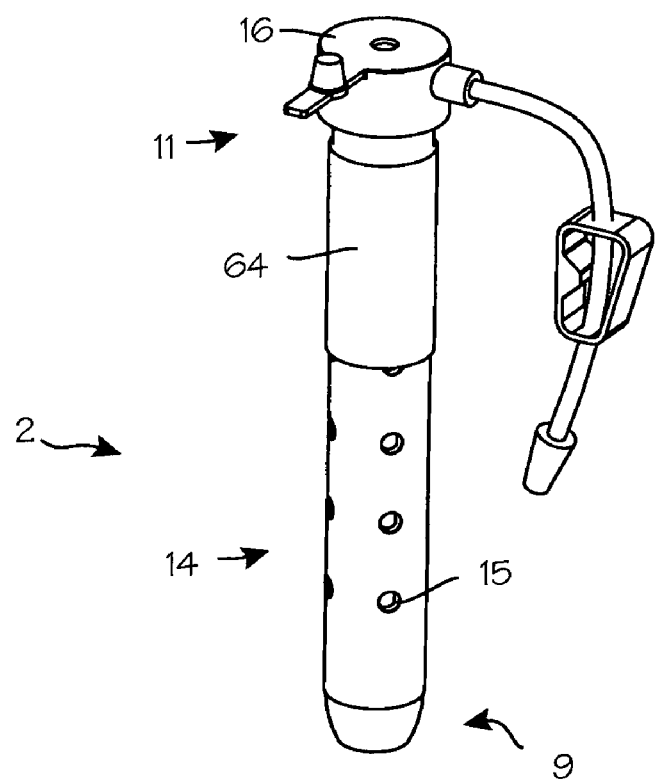
FIG. 12 illustrates an anti-extravasation minimization sheath having an inner tube, an outer tube and one or more drainage lumens disposed between the inner and outer tube.
Figure 13:
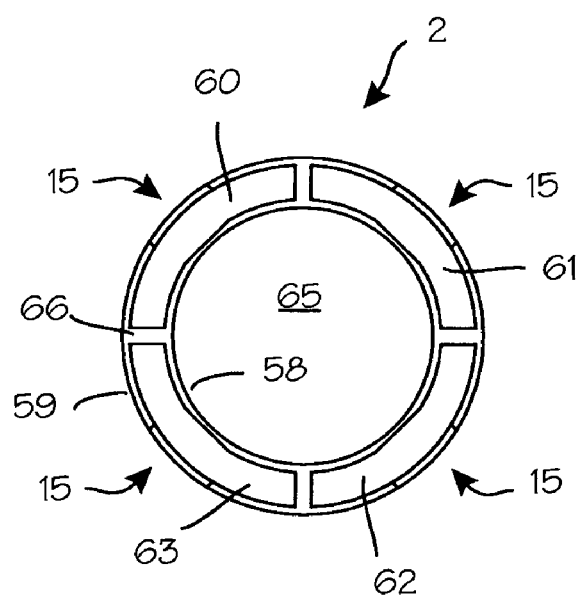
FIG. 13 illustrates a radial cross-section of an anti-extravasation minimization sheath 2 having an inner tube 58, an outer tube 59 and one or more drainage lumens 60, 61, 62 and 63 disposed between the inner and outer tube.

FIG. 12 and FIG. 13 illustrate an anti-extravasation minimization sheath 2 having an inner tube 58, an outer tube 59 and one or more drainage lumens 60, 61, 62 and 63 disposed between the inner and outer tube. A plurality of drainage apertures 15 are disposed in the central portion 14 or body of the outer tube. The drainage apertures are disposed in such a way that the drainage apertures are placed in fluid communication with tissue surrounding a surgical field when the sheath is in use. Each drainage aperture communicates with one or more drainage lumens disposed inside the sheath, thereby allowing fluid to drain from the tissue surrounding the surgical site to sources or sinks located outside the patient. The proximal section 11 of the sheath is provided with a hub 16 or manifold allowing medical personnel to easily pull the sheath over and secure the sheath to the rigid cannula, arthroscope and/or arthroscopic instrument. The hub 16 is adapted for coupling to a drain tube in fluid communication with a vacuum source or sink. The proximal section 11 of the anti-extravasation sheath may also be provided with fittings, such as a locking hub or snap latches, that attach to fittings or openings disposed on the arthroscope or other instrument, thereby securing the sheath. A slidable sleeve 64 is disposed over the outer diameter of the sheath 2 to control exposure of the number of drainage apertures to tissue surrounding a surgical field and accommodate shoulders of varying thicknesses.

FIG. 13 illustrates a radial cross-section of an anti-extravasation minimization sheath 2 having an inner tube 58, an outer tube 59 and one or more drainage lumens 60, 61, 62 and 63 disposed between the inner and outer tube. The anti-extravasation sheath comprises an outer tube, an inner tube characterized by a central lumen 65 and a plurality of ribs 66 characterizing drainage lumens 60, 61, 62 and 63 running longitudinally within the sheath. The inner diameter of the inner tube is sized and dimensioned to closely fit over the outer diameter of an arthroscopic instrument. The sheath has a central lumen 65, bounded by the inner tube having a wall, through which the arthroscope or other arthroscopic surgical instrument is inserted. The sheath has four outer lumens 60, 61, 62 and 63 bounded by the wall of the inner tube 58, the wall of the outer tube 59 and four relatively stiff ribs 67 that extend between the inner and outer tubes and that run along the length of the sheath. The distal end 9 of the sheath in the area of the outer lumens 60, 61, 62 and 63 is sealed closed and provided with a rounded shape to help prevent injury to the patient (the central lumen remains open to accommodate the arthroscopic instrument). Drainage apertures 15 disposed in the outer allow interstitial fluids to flow out of tissue surrounding an arthroscopic surgical field or joint capsule and into the outer drainage lumens.

The anti-extravasation minimization sheath 2 can be part of a complete fluid management system comprising a fluid source, vacuum source, arthroscopic surgical pump and control system. An over pressure valve can be operably coupled to the anti-extravasation sheath to allow a drainage lumen in the device to open and drain the joint if the joint is over-pressurized by an arthroscopic pump.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A method for performing arthroscopic surgery comprising:
   providing an arthroscopic instrument suitable for performing an arthroscopic surgical procedure on a joint capsule;
   providing an anti-extravasation sheath having at least one drainage aperture disposed on a central portion of the sheath;
   disposing the arthroscopic instrument inside the sheath;
   placing a distal tip of the anti-extravasation sheath into the joint capsule such that the at least one drainage aperture is disposed within tissue surrounding an arthroscopic surgical field outside of the joint capsule;
   performing an arthroscopic surgical procedure with the arthroscopic instrument; and
   draining fluid from the tissue surrounding the arthroscopic surgical field outside of the joint capsule through the drainage aperture during the arthroscopic surgical procedure.

2. The method of claim 1 wherein the arthroscopic surgical procedure is arthroscopic shoulder surgery.

3. The method of claim 1 wherein the anti-extravasation sheath further comprises inflow/outflow holes disposed at a distal portion of the anti-extravasation sheath, the method further comprising the step locating said distal portion of the anti-extravasation sheath within the joint capsule such that the inflow/outflow holes are disposed within the joint capsule while the at least one drainage aperture is disposed within tissue surrounding an arthroscopic surgical field outside of the joint capsule, and providing fluid inflow and outflow through the inflow/outflow holes to the joint capsule.

* * * * *